United States Patent [19]
Allen

[11] 3,960,520
[45] June 1, 1976

[54] SEPARATION OF ISOMERS
[75] Inventor: Paul T. Allen, Beaumont, Tex.
[73] Assignee: Mobil Oil Corporation, New York, N.Y.
[22] Filed: Mar. 19, 1975
[21] Appl. No.: 559,842

[52] U.S. Cl.................................. 55/59; 55/67; 55/75
[51] Int. Cl.² .................. B01D 53/04; B01D 15/08
[58] Field of Search ............... 55/59, 61, 62, 75, 67; 208/310; 260/674 SA

[56] References Cited
UNITED STATES PATENTS

| | | | |
|---|---|---|---|
| 3,109,722 | 11/1963 | Dow .................................. | 55/62 X |
| 3,177,631 | 4/1965 | Tamora .............................. | 55/61 X |
| 3,699,182 | 10/1972 | Cattanach .......................... | 55/67 X |
| 3,724,170 | 4/1973 | Allen et al. ........................ | 55/67 |

*Primary Examiner*—John Adee
*Attorney, Agent, or Firm*—C. A. Huggett

[57] ABSTRACT

A mixture of $C_8$ aromatics, including para-xylene, meta-xylene orthoxylene and ethyl benzene, is separated by an adsorption/desorption procedure to provide rapid recovery of the valuable components. In this process, the aromatic mixture is passed through at least two adsorption zones in series, preferably containing zeolite ZSM-5 adsorbent, in which zones the meta-xylene and ortho-xylene pass through relatively uninhibited, whereas the para-xylene and ethyl benzene are adsorbed. The meta-xylene and ortho-xylene are removed and can be distilled to effect separation or can be separated as described in U.S. Pat. No. 3,656,278. According to this invention, the para-xylene and ethyl benzene in the zones are then desorbed in parallel, that is, introducing a desorbent separately to each zone and recovering desorbed aromatics separately from each.

10 Claims, 5 Drawing Figures

FIG.3C. Two-Step Desorption

SEPARATION OF ISOMERS

BACKGROUND OF THE INVENTION

1. Field of the Invention

This invention relates to a method for the separation of valuable components from a mixture of aromatic compounds and more particularly to a novel process effecting substantially complete separation of meta-xylene and ortho-xylene from a mixture containing these components together with ethyl benzene and para-xylene in a rapid and economic manner.

2. Description of the Prior Art

Aromatic compounds and particularly para-xylene, meta-xylene, orthoxylene and ethyl benzene are well known as very useful materials in the chemical industry but are generally found only in admixture with each other. For example, they are found in substantial quantities in coke oven light oil, in reformed petroleum naphthas and in "pyrolysis gasoline" from steam cracking of hydrocarbons to make olefins. Over the years many processes have been devised for separation of the several components to recover the desired components of satisfactory purity. Those techniques are in use on a large scale. Present practices employ distillation, selective sorption or fractional crystallization or combinations of those unit processes. Distillation is difficult and very expensive because of the very close boiling points of the components. Among the sorption processes, proposals have been offered for chromatography and sorption/desorption processes.

The use of zeolite ZSM-5 for separation of $C_8$ aromatics is disclosed in certain prior patents assigned to the assignee of this application. See U.S. Pat. Nos. 3,653,184; 3,656,278; 3,698,157; 3,724,170; 3,729,523; 3,760,024 and 3,770,841. A system for achieving continuity of flow by parallel systems is shown in copending application Ser. No. 310,054, filed Apr. 28, 1972. In the processes of these prior patents and application the adsorption capabilities of the zeolite are utilized to effect production chromatography or adsorption and then desorption of the components of the aromatic mixture. Since the filing of the applications of reference, however, it has been realized that the time required to effect adsorption of each component followed by desorption of each component is expensive in both capital cost and operating cost. A matter of primary importance in this regard is that desorption is much more time consuming than adsorption, all as developed more fully below. Accordingly, work has continued in this area in an effort to uncover procedures by which the adsorption characteristics of ZSM-5 zeolites can be utilized to best advantage while obtaining a rapid separation of the desirable components. It is found that the apparatus employed in the chromatographic process of U.S. Pat. No. 3,724,170 is susceptible of modification to a sorption/desorption mode which provides an effective method of series adsorption and parallel desorption for rapid separation and recovery of the $C_8$ aromatic components.

In the prior patents held by the assignee of this application and in the general prior art relating to a separation of $C_8$ aromatics by selective sorption, two distinct modes of operation need to be distinguished by their process characteristics, their advantages and their disadvantages.

CHROMATOGRAPHIC MODE

Production chromatography is characterized by continuous flow through a sorbent of a carrier gas, e.g. nitrogen, helium or steam. Pulses of the charge mixture to be separated are introduced to the feed end of a columnar bed with the carrier gas at suitable intervals. As the charge pulse moves through the column, each component is delayed by a factor related to the relative strength of its sorption bond to the sorbent. The components thus become separated and demarcation between successive portions of differing components become better defined as the pulse of charge moves along the column. A detector at the column outlet can thus operate to divert the effluent to different receivers for the several components.

This system is very effective to make sharp separations of the several components but requires very large volumes of sorbent per unit volume of charge because a major portion of sorbent volume is occupied by carrier gas. It may be noted that a significant portion of sorbent volume is occupied solely by carrier gas as separation between two successive pulses of charge.

SORPTION MODE

Many processes for selective sorption operate by loading the sorbent bed in its entirety with a portion of the charge which it is desired to separate and then recovering the sorbed component of components by heating, reduction of pressure or contacting with a stream of desorbent gas or liquid or a combination of such techniques. According to this technique, the charge mixture is flowed into the sorbent bed, usually without carrier gas. The component or components least strongly sorbed appear as the first effluent of the operation. As feed of the charge continues, the most strongly sorbed components displace that portion of the less strongly sorbed components which may have been sorbed until the system approaches the capacity of the sorbent to retain the most strongly sorbed component(s), i.e. the sorbent is "loaded" with such component(s). At this time, the strongly sorbed material can be detected in the effluent. General practice is to discontinue feed and desorb the bed by passage therethrough of a stripping gas at increased temperature to recover the sorbed product.

As with operation by chromatographic mode, sharp separations are obtained only at considerable expense. In sorption mode operation, the problem is that desorption is very slow compared with the sorption part of the cycle. Desorption requires a period which is more than a full order of magnitude greater than the sorption side of the cycle, e.g. thirty times as long.

SUMMARY OF THE INVENTION

The broad aspects of the invention are aptly considered with respect to the significant advance described in U.S. Pat. No. 3,724,170, the disclosure of which is hereby incorporated by reference. Operating in a chromatographic mode, the process of that patent takes advantage of the fact that zeolite ZSM-5 tends to first separate a mixture of $C_8$ aromatics into two fractions: a mixture of ortho-xylene and meta-xylene (hereafter OX and MX, respectively) and a mixture of para-xylene and ethyl benzene (hereafter PX and EB, respectively).

By separating the sorption column into two parts as taught in that patent, the undesired OX and MX are taken off in admixture at a point between the two parts of the column. The mixture of EB and PX passes to the second part of the column, free of OX and MX, thus greatly reducing the load on the portion of the whole responsible for the separation between EB and PX, with resultant economies in capital investment and operating expenses.

The present invention also takes advantage of ZSM-5 capability to make a first separation to two mixed streams of OX plus MX and EB plus PX and the capability of that zeolite to obtain a sharp separation between EB & PX. The invention further takes advantage of the fact that EB & PX are not evenly distributed along the line of flow in that portion of sorbed aromatics made up of EB & PX.

According to one embodiment of this invention, a $C_8$ aromatics mixture is contacted in sorption mode with ZSM-5 sorbent in a column having at least two portions in series during sorption. Upon detecting that the series portions are loaded with EB and PX, the portions are desorbed in parallel to provide EB-PX mixtures of different composition. Those mixtures are preferably partitioned in separate operations, each designed (e.g. length and diameter of bed) for the composition of the mixture handled. A preferred type of partition of the EB-PX mixtures is by chromatographic separation over ZSM-5 type zeolite. The OX-MX mixture recovered as effluent of the first stage (sorption mode) may be isomerized in known manner to generate additional PX and the isomerizate returned to feed for the process of this invention. Alternatively, that mixture may be easily distilled to separate its components since their boiling points differ by more than five degrees, Centigrade.

It is accordingly one object of the present invention to provide a process for the separation of a $C_8+$ aromatics mixture which contains xylene isomers and ethyl benzene which overcomes or otherwise mitigates the problems of the prior art.

A further object of the invention is to provide a procedure whereby ortho-xylene and meta-xylene may be effectively and rapidly separated from a $C_8-$ aromatics mixture utilizing adsorption in series and desorption in parallel.

Other objects and advantages of the present invention will become apparent as the description thereof proceeds.

In satisfaction of the foregoing objects and advantages there is provided by this invention a process for the separation and recovery of ethyl benzene and the xylene isomers from a $C_8+$ aromatic mixture containing the same which comprisies: contacting the $C_8+$ aromatic mixture with a ZSM-5 zeolite in a sorption column whereby the para-xylene and ethyl benzene are adsorbed, and unadsorbed effluent comprising substantially meta-xylene and ortho-xylene is removed for separation and the adsorbed components are then desorbed to recover a mixture of para-xylene and ethyl benzene, the adsorption being carried out in series and the desorption being carried out in parallel.

It will be apparent that two or more columns of sorbent acting in series behave as a single column of a length equal to sum of the lengths of the several serial columns. The reason for physical separation of the columns is solely to facilitate parallel desorption which decreases desorption time. Other techniques for achieving that result can be substituted within the scope of the invention.

Parallel desorption of the first stage sorption mode may be conducted by flow of stripping gas in the same direction as the flow during sorption or it may be in reverse direction or at right angles to the sorption flow. When desorption flow is normal to the direction of sorption flow, the time of desorption can be greatly reduced by using a column of high length to diameter ratio.

The nature of the invention and the variances to which it is susceptible will be apparent from the annexed drawings when considered in conjunction with the description of preferred embodiments below.

DESCRIPTION OF PREFERRED EMBODIMENTS

Figure 1:
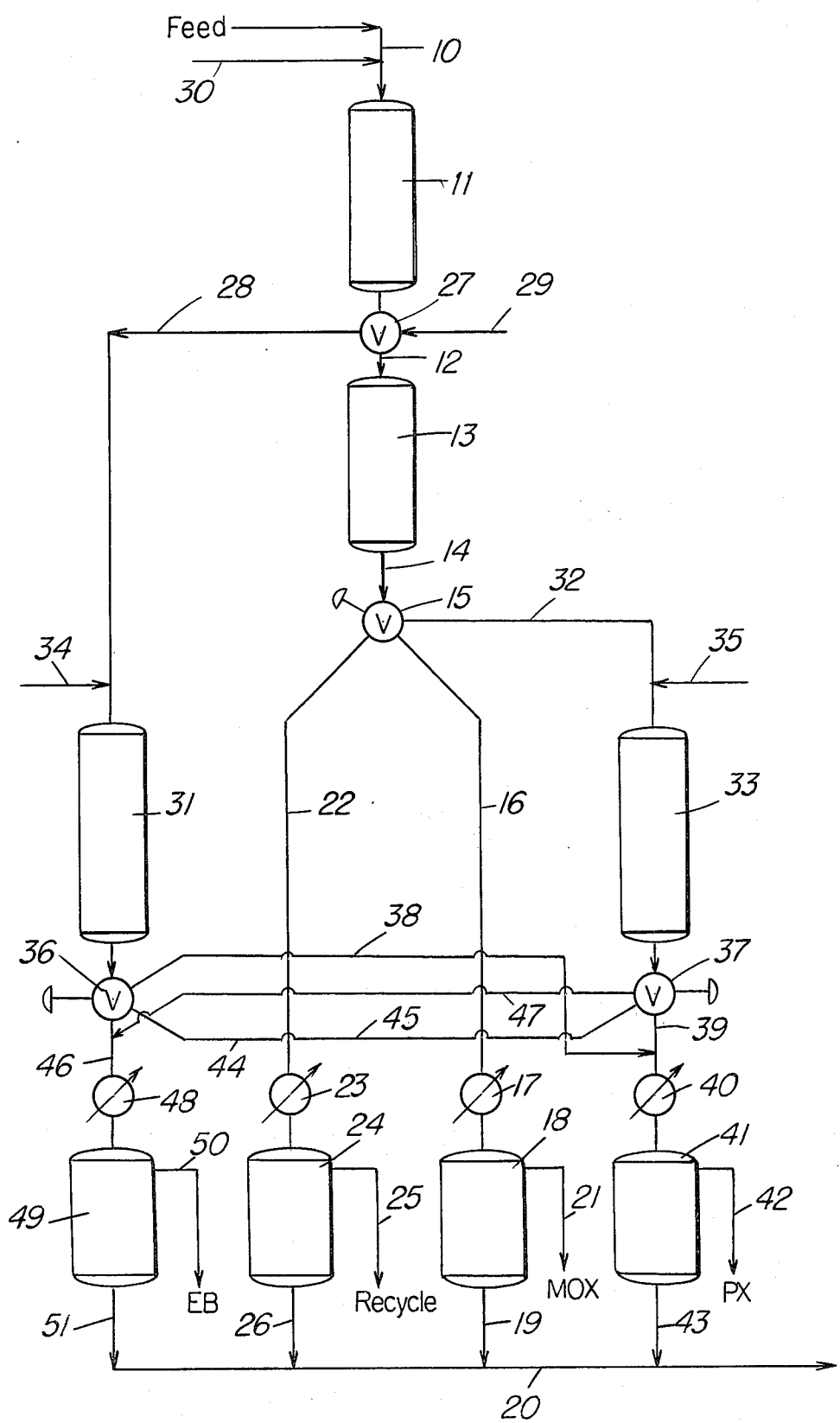
FIG. 1 is a diagrammatic representation of equipment and process flow for practice of the invention.

As shown in FIG. 1, a stream of $C_8$ aromatics feed is introduced by line 10 to flow though beds of sorbent serially arranged in a first sorption column 11 and thence through a connecting pipe 12 into a second sorption column 13. Effluent leaves the series of sorption beds by line 14.

Sorption is continued with discharge of MX and OX through a multiport valve 15 until the first traces of para-xylene are detected by a conventional detector, not shown. The mixture MX-OX (hereinafter MOX) passes by by line 16 through a condenser 17 to receiver 18. Any water present, as by displacement of sorbed water from the stripping operation described hereinafter, is separated by decantation in receiver 18 and passed by line 19 to desorbent recycle line 20. MOX is withdrawn at line 21.

Upon detection that para-xylene is appearing in the effluent of the series sorption columns, the effluent is diverted by the multi-port valve to line 22 through condenser 23 into receiving decanter 24 from which a stream is decanted at line 25 to be recycled to sorption feed. This recycle will contain MX, OX and PX. Any water in vessel 24 is withdrawn for recycle at line 26.

Upon discontinuing flow of the mixed stream to receiver 24, the vessels 11 and 13 are now loaded with EB and PX with the majority of the EB in vessel 11 and the majority of the PX in the vessel 13. The system is now placed on parallel desorption by rotating valve 27 such that effluent of vessel 11 will pass by line 28 and that desorbent, preferably steam, will be introduced by line 29 to the inlet of vessel 13. Supply of $C_8$ aromatics feed by line 10 is discontinued and desorbent is introduced by line 30 to the inlet of vessel 11.

As desorbent is passed through vessel 11 from line 30, it displaces the aromatics sorbed in vessel 11 to be discharged with the desorbent through line 28 to chromatographic column 31. The effluent of vessel 13 at this stage is $C_8$ aromatics displaced from the sorbent in vessel 13 and passed by line 32 to chromatographic column 33 through suitable adjustment of value 15.

The chromatographic columns 31 and 33 are operated in similar manner, differing only in the relative proportions of EB and PX handled by each column. A constant stream of carrier gas, preferably also steam, is introduced by lines 34 and 35. A pulse of aromatics feed passes to each of the chromatographic columns at the time of desorbing the vessels 11 and 13.

As a general rule, it is found that a trace of MOX "tails out" in the PX, EB mixture desorbed from columns 11 and 13. That trace of MOX is detected and diverted to vessel 18 through a pipe not shown in order to achieve maximum purity of PX and EB. Following removal of the trace of MOX from the chromatographic columns 31 and 33, the mixture of PX and EB introduced thereto is further separated by the normal selection delay such that PX is discharged first, followed by EB. The effluents from chromatographic columns 31 and 33 pass to multi-port valves 36 and 37 respectively under control of conventional detectors, not shown. The first major effluent of each column is PX which passes by lines 38 and 39 through a condenser 40 to a decanting receiver 41. PX is withdrawn by line 42 at high purity and desorbent passes to recycle by line 43.

At first detection of EB in the effluent of columns 31 and 33, the appropriate valves 36 or 37 is operated to divert a slop stream by lines 44 and 45 to recycle decanter 24. The remaining effluent from chromatographic columns 31 and 33 is passed in like manner by lines 46 and 47 through condenser 48 and decanting receiver 49 from which high purity EB is withdrawn by line 50 while recovered desorbent passes by line 51 to desorbent recycle.

Figure 2:
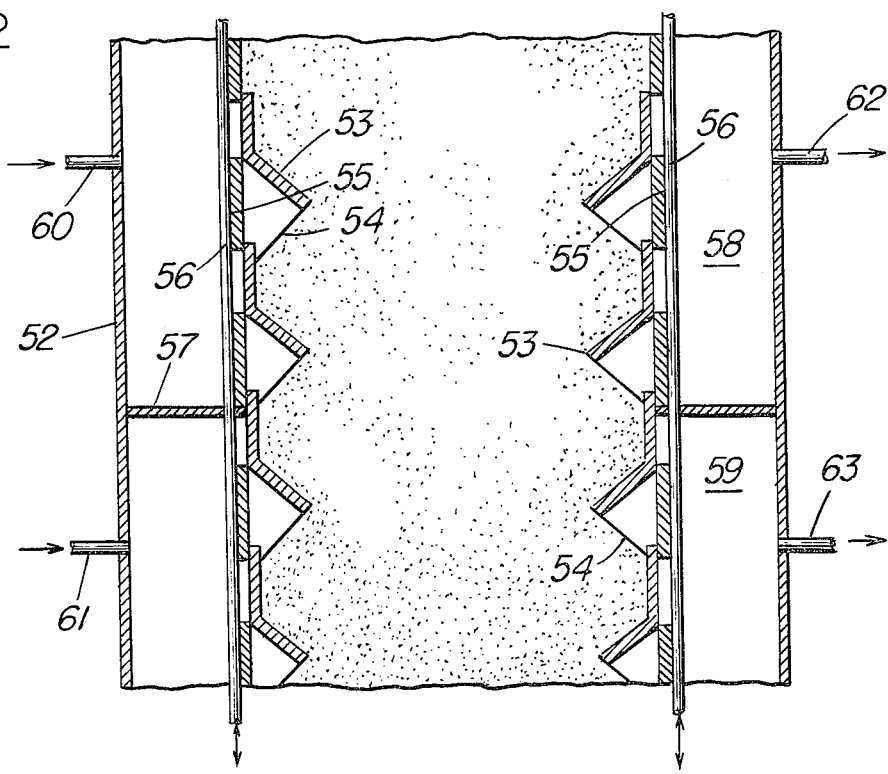
FIG. 2 is a partial elevation in section of apparatus for desorption by flow normal to the direction of sorption flow.

Referring now to FIG. 2, the sorption mode stage may be set up for desorption by flow normal to the sorption flow using apparatus here shown in fragmentary section. The sorption and desorption stages are carried on within a shell 52 having the sorbent contained therein by louvres 53 arranged such that the granular sorbent will lie at an angle of repose indicated at 54 to avoid loss of sorbent from the sorption column. The openings between the louvres are closed during the sorption stage by a series of gates 55 operated by a rod 56 attached thereto. When it is desired to desorb the vessel, the rod 56 is moved upwardly to open the spaces between louvres for flow of desorption gas across the width of the vessel.

Preferably this vessel is also set up for segregating desorbed streams of varying proportions of EB and PX. A partition 57 divides the space just inside shell 52 into an upper plenum chamber 58 and a lower plenum chamber 59. Desorbent is introduced by pipe 60 and pipe 61 to pass across the column and displace sorbed aromatics to the plenum chambers 58 and 59 from which they are withdrawn by pipes 62 and 63 respectively.

Figure 3A:
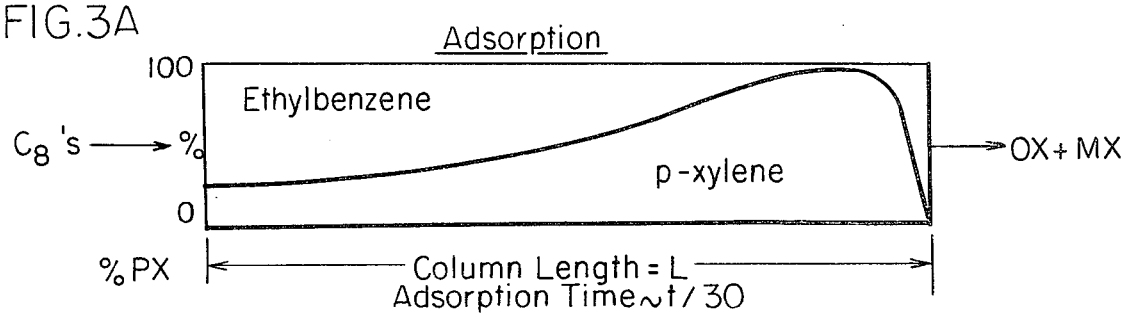
FIG. 3 is a series of three graphic representations illustrative of the advantages of the invention.
Figure 3B:
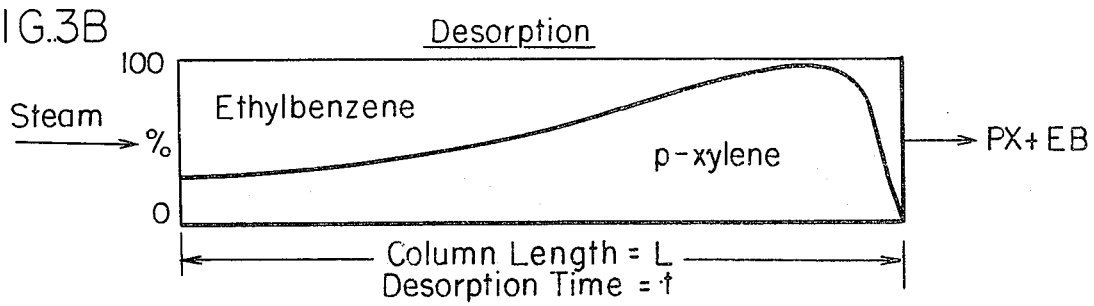
Figure 3B:
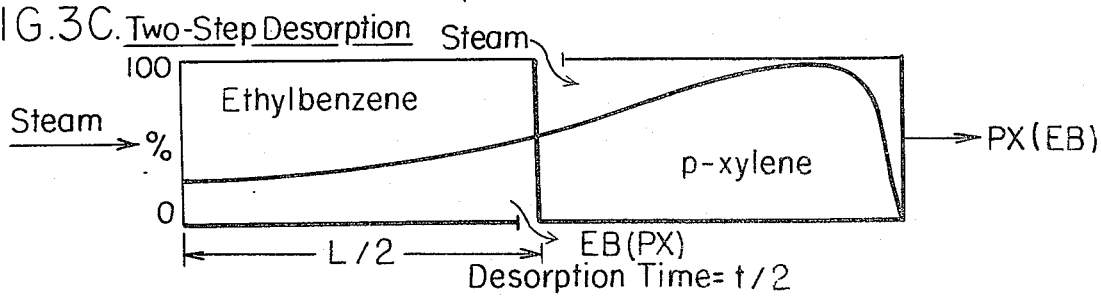

The nature of results obtained is illustrated graphically in FIG. 3. FIG. 3A represents the sorption step at the time when the sorbent becomes loaded with EB and PX, OX and MX having left the column. As will be noted from the shape of the curve, PX is concentrated near the outlet of the column, while the majority of EB is concentrated near the inlet to the column. If desorption is conducted by passing steam from end to end of the column, (FIG. 3B) there is obtained a mixture of PX and EB which has the concentrations representing the average throughout the column. The desorption time is about thirty times as long as the sorption part of the cycle and, in effect, determines length of the cycle before the column is again placed on sorption.

FIG. 3C represents desorption of two sections of the bed in parallel. Since the length of each desorbed portion is only half the total length of the bed, desorption takes only half the time required when operating according to FIG. 3B. In addition, the two desorbed streams contain EB and PX in different concentrations, EB being predominant in the stream from the first part of the bed and PX being predominant from the second half of the bed. Chromatographic separation of PX and EB from these two streams in separate chromatographic columns is greatly simplified.

It will be understood from this description that the process provides unique advantages in the separation of $C_8$ aromatic isomers. Thus the concept clearly enhances the attractiveness of a $C_8$ aromatics separation with zeolite ZSM-5 or zeolite ZSM-11.

In a sorption process, the throughput is determined by the amount of feed that the packing can separate per charge multiplied by the number of feed charges that can be separated per unit time divided by the packing weight as follows:

$$\text{Throughput, g feed/hr/g packing} = \frac{\text{(g feed/charge) (No. of charges/hr)}}{\text{g packing}}$$

The amount of $C_8$ aromatics feed that a column can separate per charge is determined by several factors:
1. Adsorbent capacity at column oven temperature
2. Adsorbent selectivity for adsorbing the desorbent gas relative to para-xylene (or ethyl benzene)
3. Gas flowrate
4. Feed composition, amount of adsorbable components
5. Condition of column, including packing particle size and column efficiency
6. Column geometry The optimum conditions of column over temperature, gas flowrate, packing particle size and range, column diameter and length and other parameters will therefore set the amount of feed that can be separated per charge. The only other variable open to increasing throughput is the number of feed charges per unit time. (decreased cycle time). Cycle time is the time required for adsorption and desorption of para-xylene and ethyl benzene. Adsorption time is insignificant compared to desorption time as desorption time is determined to a large extent by column oven temperature, gas flowrate and column length. By decreasing the desorption time, a greater number of feed charges per hour can be made. Thus the present invention provides a procedure whereby the desorption time can be substantially reduced.

As pointed out above, the separation of the $C_8$ components is carried out in a sorption mode utilizing an adsorbent which will adsorb substantially only the para-xylene and ethyl benzene but not the other components of the mixture. The preferred absorbents to effect these separations are certain crystalline aluminosilicate zeolite molecular sieves which have the desired properties. Preferred zeolites are the zeolites ZSM-5 and ZSM-11 zeolites described in U.S. Pat. Nos. 3,702,886 and 3,709,979, respectively. These zeolites are characterized by very high ratios of silica to alumina, up to 200 to 1 and higher. More preferred are ZSM-5 and ZSM-11 zeolites which have been reacted with certain silanes as described in U.S. Pat. No. 3,698,157.

The temperature at which the separations are carried out is also important; thus, temperatures ranging from about 100°C. to about 250°C. should be used. It should be noted that a wider temperature range can be employed but because of the possibility of catalytic conversion in the zeolitecontaining column, 250°C. appears to be a suitable upper limit. A more preferred temperature range is between about 100° to 200°C.

As indicated above, the zeolites preferably utilized in the separation are of a special type and are disclosed and claimed for use in a novel zeolite chromatographic process in U.S. Pat. No. 3,699,182 of J. Cattanach of the same assignee. Generally, these zeolitic materials allow selective separations to be achieved depending on either the size, shape or polarity of the sorbate molecules. This class of novel crystalline aluminosilicates can generally be stated to have intermediate shape-selective sorption properties. The unique nature of this novel class of zeolites is characterized by the presence of uniform pore openings which are apparently elliptical rather than circular in nature. The effective pore openings of this unique class of zeolites have both a major and a minor axes, and it is for this reason that the unusual and novel molecular sieving effects are achieved. The unique type of molecular sieving produced has generally been referred to as a "keyhole" molecular sieving action. From their dynamic molecular sieving properties it would appear that the major and minor axes of the elliptical pore in this family of zeolites have effective sizes of about 7.0 ± 0.7A and 5.0 ± 0.5A, respectively.

This general family of zeolites are described as ZSM-5 type compositions. In general, they have a characteristic X-ray diffraction pattern set forth in the patents cited above. ZSM-5 compositions can also be identified, in terms of mole ratios of oxides, as follows:

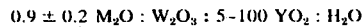
$$0.9 \pm 0.2\ M_nO : W_2O_3 : 5\text{-}100\ YO_2 : H_2O$$

wherein M is a cation, n is the valence of said cation, W is selected from the group consisting of aluminum and gallium, Y is selected from the group consisting of silicon and germanium, and Z is from 0 to 40. In a more preferred synthesized form, the zeolite has a formula, in terms of mole ratios of oxides, as follows:

$$0.9 \pm 0.2\ M_{2/n}O : Al_2O_3 : 5\text{-}100\ SiO_2 : z\ H_2O$$

and M is selected from the group consisting of a mixture of alkali metal cations, especially sodium, and tetraalkylammonium cations, the alkyl groups of which preferably contain 2-5 carbon atoms.

In a preferred embodiment of ZSM-5, W is aluminum, Y is silicon and the silica/alumina mole ratio is at least 10 and ranges up to about 60.

The zeolites used in the instant invention can have the original cations associated therewith replaced by a wide variety of other cations according to techniques well-known in the art. Typical replacing cations would include hydrogen, ammonium and metal cations including mixtures of the same.

Typical ion exchange techniques would be to contact the particular zeolite with a salt of the desired replacing cation or cations. Although a wide variety of salts can be employed, particular preference is given to to chlorides, nitrates and sulfates.

Representative ion exchange techniques are disclosed in a wide variety of patents including U.S. Pat. No. 3,140,249, U.S. Pat. No. 3,140,251 and U.S. Pat. No. 3,140,253.

Following contact with the salt solution of the desired replacing cation, the zeolites are then preferably washed with water and dried at a temperature ranging from 150°F. to about 600°F. and thereafter calcined in air or other inert gas at temperatures ranging from about 500°F. to 1500°F. for periods of time ranging from 1 to 48 hours or more.

Prior to use, the zeolites should be dehydrated at least partially. This can be done by heating to a temperature in the range of 200° to 600°C. in an atmosphere, such as air, nitrogen, etc. and at atmospheric or subatmospheric pressures for between 1 and 48 hours. Dehydration can also be performed at lower temperatures merely by using a vacuum, but a longer time is required to obtain a sufficient amount of dehydration.

In practicing the process, it may be desired to incorporate the zeolite with another material resistant to the temperatures and other conditions employed in the separation processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides.

Naturally occurring clays which can be composited with the zeolites include the montmorillonite and kaolin family, which families include the sub-bentonites, and the kaolins commonly known as Dixie, McNamee, Georgia and Florida clays or others in which the main mineral constitutent is halloysite, kaolinite, dickite, nacrite, or anauxite. Such clays can be used in the raw state as originally mined or intially subjected to calcination, acid treatment or chemical modification.

In addition to the foregoing materials, the ZSM-5 type zeolites can be composited with a porous matrix material such as alumina, silicaalumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. The relative proportions of finely divided crystalline aluminosilicate ZSM-5 and inorganic oxide gel matrix vary widely with the crystalline aluminosilicate content ranging from about 1 to about 99 percent by weight. A preferred composite is a minor amount of alumina, about 20 weight percent, with the balance being zeolite.

Another embodiment of this invention resides in subjecting the zeolite ZSM-5 type to a mile steam treatment carried out at elevated temperatures of 800°F. to 1500°F. and preferably at temperatures of about 1000°F. to 1400°F. The treatment may be accomplished in an atmosphere of 100 percent steam or in atmosphere consisting of steam and a gas which is substantially inert to the aluminosilicate. The steam treatment apparently provides beneficial properties in the aluminosilicate compositions and can be conducted before, after or in place of the calcination treatment.

Even more highly preferred adsorbents are ZSM-5 and ZSM-11 zeolites which have been treated or contacted with a silane compound as superior results are achieved using these products as adsorbents. The organic substituted silanes deemed useful in the process of the present invention are those of the following general formula:

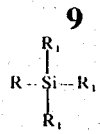

wherein, in the above formula, R is an organic radical as described hereinafter and each $R_1$ is also an organic radical such as those defined below for the group R, a hydrogen atom or a halogen atom such as chlorine or bromine. Organic radicals which may be R or $R_1$ include alkyl of 1 and more preferably up to about 40 carbon atoms, alkyl or aryl carboxylic acid acyl wherein the organic portion of said acyl group contains about 1 to 30 carbon atoms and said aryl group contains about 6 to 24 carbon atoms, aryl groups of about 6 to 24 carbons, which may also be further substituted, alkaryl and aralkyl groups containing about 7 up to about 30 carbon atoms. Highly preferred compounds falling within the above structure are those wherein R is alkyl of about 12 to 24 carbon atoms, i.e., the long chained alkyl groups, and each $R_1$ is hydrogen or chlorine. Highly preferred silanes are octadecyltrichlorosilane and dodecyltrichlorosilane. Organic silanes of the type useful in the process of the present invention are known in the art and may be prepared by known methods. For example, the tetrachloro substituted silane, $SiCl_4$, may be prepared by the reaction of chlorine and silica and the resulting product may then be reacted with the desired number of moles of a metal salt of the organic compound containing the radical for R or $C_1$ desired, by heating. Other silanes employed in the process of the present invention may be prepared by similar procedures, all of which are well known in the art.

The desired silane is then contacted with a zeolite of the type described hereinbefore, one requirement of the zeolite being that it have an available hydrogen for reaction. The silane should be selected so that steric hindrance problems are avoided. Thus in the above formula, R and only two $R_1$ should be organic radicals which means that at least one $R_1$ should be halogen.

The selected silane and the crystalline aluminosilicate zeolite are contacted in the preferred procedure at an elevated temperature. Preferably, the silane and zeolite are contacted on a weight basis of about 1:5 to 5:1, preferably about 1:2 to 1:1, respectively. It is also preferable that a binder for the zeolite be employed such as, for example, bentonite. For good contact between the reactants, it is also preferble to employ a reaction medium. Satisfactory reaction media include the esters, aliphatic hydrocarbons and halo-substituted aliphatic hydrocarbons of 5 to about 8 carbon atoms, (e.g., n-heptane), the aromatic, halo-substituted aromatic hydrocarbons and nitrogen containing compounds such as heterocyclics. A particularly preferred media is pyridine.

The following examples are presented to illustrate the invention but it is not to be considered as limited thereto. In the examples and throughout the specification parts are by weight unless otherwise indicated.

EXAMPLES 1-3

Typical preparations of ZSM-5 type zeolites are shown in these examples. Examples 1-3 show the preparation of the hydrogen form ZSM-5 and they involve the use of tetrapropylammonium hydroxide (TPAOH) or bromide (TPABR). Reaction conditions and results are shown in Table I.

EXAMPLE 4

In this example 30 parts of ZSM-5 crystalline aluminosilicate zeolite comprising 80 parts ZSM-5 and 20 parts bentonite binder, were refluxed with octadecyltrichlorosilane in a weight ratio of 1:1 in 200 cc normal-heptane solvent for a period of four hours. Thereafter the resulting solid product was recovered by decantation, the solid washed first with chloroform, then with normal-pentane and then dried at a temperature of 125°C. for 4 hours.

EXAMPLE 5

The aromatic mixture employed as the feedstock in this example was a mixture containing 15 weight percent ethyl benzene, 17.5 weight percent para-xylene,

TABLE I

| Example | 1 | 2 | 3 |
|---|---|---|---|
| Reaction Composition | 30 g $NaAlO_2$<br>720 g Ludox<br>1025 g 2.2N TPAOH | 281 g Silica-Alumina Gel Fines<br>3.3 lb TPABr Solution | 0.56 lb $NaAlO_2$<br>44.7 lb Sodium Silicate<br>5.6 lb TPABr<br>16.7 lb NaCl<br>4.5 lb $H_2SO_4$<br>132.0 lb $H_2O$ |
| Reaction Temperature (°C) | 150 | 100 | 100 |
| Time (hour) | 168 | 168 | 327 |
| | —————Washed dried at 230°F., calcined 16 hrs. at 1000°F.————— | | |
| Base Exchange | —————————$NH_4Cl$ Solution——————— | | |
| Conc. (Wt.%) | 25 | 5 | 25 |
| Temp. (°C) | 90 | 25 | 90 |
| Contacts | ×3 | ×4 | ×3 |
| Pelleted | | | |
| Calcined (hr) | 16 | 10 | 16 |
| (°F) | 1000 | 1000 | 1000 |
| Steamed (hr) | 14 | 24 | 14 |
| (°F) | 1290 | 1200 | 1290 |
| (psia) | 15 | 30 | 15 |
| Chemical Composition (g/100g) | | | |
| Na | 0.08 | 0.23 | 0.02 |
| $Al_2O_3$ | 4.7 | 2.2 | 3.0 |
| $SiO_2$ | 96.9 | 95.3 | 94.8 |
| X-ray type | ZSM-5 | ZSM-5 | ZSM-5 |

42 weight percent meta-xylene and 25.5 weight percent ortho-xylene. This mixture was vaporized at the rate of 2.16 grams per minute and passed through the column at a temperature of 400°F. without carrier gas for 60 minutes. The column was 1.7 inches interior diameter and 43 inches long. The column was packed with 1/32 inch extrudate of zeolite ZSM-5 in an alumina matrix.

The column was provided with an extrance and an exit as well as an additional entrance and exit for desorbent steam during desorption.

As the stream of feedstock was pulsed through the column, one gram samples were collected and analyzed. When the analysis indicated that the amount of para-xylene in the stream emanating from the column began to show a noticeable increase, the feed was stopped. As this point, 129.6 grams of feedstock had been introduced into the column and 88.6 grams, a mixture of meta-xylene and ortho-xylene, had been removed from the exit end of the column. The remainder of the starting mixture remained adsorbed in the column.

At this point, two streams of desorbent steam were introduced into the column, one stream at the entrance to the column and the second stream at a point midway of the column. The exit point for the first stream was at a point midway of the column or near the entrance point of the second stream. The exit point for the second stream was at the exit end of the column. The two stream were combined, condensed and decanted to remove the water for recycle and yield a mixture of 31.5 grams of ethyl benzene and para-xylene.

In this example desorption of the column was accomplished in about one-half the time usually required for desorption of a column of this size, thus greatly increasing the efficiency of the system.

In describing the process of this invention, the word "adsorbed" has been used in a relative sense. Thus in the specification and claims, the terms "adsorbed" and "hot adsorbed" should be understood to mean "preferentially adsorbed" and "preferentially not adsorbed" since such adsorptions in chromatographic systems such as this do not always occur in the extent of absolutely complete absorption.

The invention has been described herein with reference to certain preferred embodiments, however, as obvious variations thereon will become apparent to those skilled in the art the invention is not to be considered as limited thereto.

I claim:

1. In a method for the separation and recovery of the isomers contained in an aromatic mixture comprising para-xylene, meta-xylene, ortho-xylene and ethyl-benzene to separate this mixture into one stream comprising meta-xylene and ortho-xylene and a second stream comprising para-xylene and ethyl benzene, by a process which includes conducting said mixture through an elongated bed of zeolite adsorbent contained in a column whereby paraxylene and ethyl benzene are substantially adsorbed and meta-xylene and ortho-xylene are substantially not adsorbed, the improvement which comprises contacting said mixture in vapor phase with said zeolite adsorbent to effect adsorption of at least a major amount of the para-xylene and ethyl benzene and separately desorbing the adsorbed para-xylene and ethyl benzene simultaneously from each of a plurality of portions of said bed.

2. A method according to claim 1 wherein said starting aromatic mixture contains about 15–40 weight percent of para-xylene, about 0–15 weight percent ethyl benzene, about 0–25 weight percent ortho-xylene and about 40–60 weight percent meta-xylene.

3. A method according to claim 2 wherein said adsorption stage is conducted in the presence of the zeolite adsorber at a temperature of about 50° to 500°F.

4. A method according to claim 3 wherein the adsorbent is zeolite ZSM-5 or zeolite ZSM-11.

5. A method according to claim 4 wherein the desorbent is steam.

6. A method according to claim 1 wherein the desorbent is introduced as a first stream at one end of the bed and as a second stream at one point intermediate the ends of the bed, the first desorbent stream being removed at a point intermediate the ends of the bed and the second stream at the end of the column bed remote from the end at which said first stream is introduced.

7. A method according to claim 6 wherein desorbent is introduced at one end of the bed and at least two points along the length of the column and separate exit points are provided for each desorbent stream.

8. A method according to claim 5 wherein the desorbent stream is processed to remove the desorbent gas which is recycled to the system and there is removed a mixture of para-xylene and ethyl benzene.

9. A method according to claim 1 wherein streams of para-xylene mixed with ethyl benzene desorbed from different portions of the bed are resolved into their components by chromatographic separation.

10. A method according to claim 9 wherein the sorbent in said chromatographic separation in zeolite ZSM-5 or zeolite ZSM-11.

* * * * *

UNITED STATES PATENT AND TRADEMARK OFFICE
CERTIFICATE OF CORRECTION

PATENT NO. : 3,960,520
DATED : June 1, 1976
INVENTOR(S) : PAUL T. ALLEN

It is certified that error appears in the above-identified patent and that said Letters Patent are hereby corrected as shown below:

| | |
|---|---|
| Column 8, line 38 | "silicaalumina" should be --silica-alumina-- |
| Column 8, line 51 | "mile" should be --mild-- |
| Column 11, line 22 | "stream" should be --streams-- |
| Column 11, line 32 | "hot adsorbed" should be --not adsorbed-- |
| Column 12, line 39 | "removed" should be --recovered-- |
| Column 12, line 46 | "in zeolite" should be --is zeolite-- |

Signed and Sealed this

Twelfth Day of October 1976

[SEAL]

Attest:

RUTH C. MASON
*Attesting Officer*

C. MARSHALL DANN
*Commissioner of Patents and Trademarks*